(12) United States Patent
Pavcnik et al.

(10) Patent No.: US 7,871,430 B2
(45) Date of Patent: Jan. 18, 2011

(54) MEDICAL DEVICE DELIVERY SYSTEM

(75) Inventors: Dusan Pavcnik, Portland, OR (US);
Christopher G. Dixon, Bloomington, IN (US); Jacob A. Flagle, Indianapolis, IN (US); Mike Garrison, Bloomington, IN (US); Andrew K. Hoffa, Bloomington, IN (US); Ray Leonard, II, Bloomington, IN (US); Brian C. Case, Bloomington, IN (US)

(73) Assignees: Cook Incorporated, Bloomington, IN (US); Oregon Health & Science University, Portland, OR (US)

( * ) Notice: Subject to any disclaimer, the term of this patent is extended or adjusted under 35 U.S.C. 154(b) by 1748 days.

(21) Appl. No.: 10/307,141

(22) Filed: Nov. 27, 2002

(65) Prior Publication Data

US 2003/0144670 A1     Jul. 31, 2003

Related U.S. Application Data

(60) Provisional application No. 60/338,714, filed on Nov. 29, 2001.

(51) Int. Cl.
    *A61F 2/06* (2006.01)
(52) U.S. Cl. .................................. 623/1.11; 623/1.12
(58) Field of Classification Search .............. 623/1.11, 623/2.11, 1.15, 1.13, 1.23, 1.12, 108; 606/200, 606/194, 108; 128/898; 604/96.01, 103.1, 604/264, 101.03; 523/124
    See application file for complete search history.

(56) References Cited

U.S. PATENT DOCUMENTS

| | | | |
|---|---|---|---|
| 4,494,531 A | 1/1985 | Gianturco | |
| 4,619,246 A | 10/1986 | Molgaard-Nielsen et al. | |
| 4,665,918 A | * 5/1987 | Garza et al. | 606/108 |
| 5,133,733 A | 7/1992 | Rasmussen et al. | |
| 5,163,953 A | 11/1992 | Vince | |
| 5,201,757 A | * 4/1993 | Heyn et al. | 606/198 |

(Continued)

FOREIGN PATENT DOCUMENTS

EP     0346564     12/1989

(Continued)

OTHER PUBLICATIONS

U.S. Appl. No. 09/777,091, filed Feb. 5, 2001; Published No. US-2001-0039450-A1.

(Continued)

*Primary Examiner*—Todd E Manahan
*Assistant Examiner*—Diane Yabut
(74) *Attorney, Agent, or Firm*—Buchanan Nipper (57) ABSTRACT

A delivery system (10) for implanting a medical device (30) such as a venous valve into the vasculature of a patient. The delivery system includes a delivery catheter (11) having a device-containing portion (15) adjacent to the distal end (14) thereof, and an inner member (16) extending through the catheter and beyond the distal end thereof, to an atraumatic distal tip portion (17) forward of the catheter distal end. The inner member extends through the medical device in the device-containing region, includes a proximal portion (18) with a sufficiently large diameter to prevent longitudinal movement of the device as the catheter is retracted during deployment, and centers the device upon release from the distal catheter end during deployment.

8 Claims, 11 Drawing Sheets

U.S. PATENT DOCUMENTS

| | | | |
|---|---|---|---|
| 5,324,304 A | | 6/1994 | Rasmussen |
| 5,329,942 A | | 7/1994 | Gunther et al. |
| 5,534,007 A | | 7/1996 | St. Germain et al. |
| 5,571,168 A | * | 11/1996 | Toro .................... 623/1.11 |
| 5,603,698 A | * | 2/1997 | Roberts et al. .......... 604/104 |
| 5,830,209 A | * | 11/1998 | Savage et al. ............ 606/15 |
| 5,843,090 A | * | 12/1998 | Schuetz .................. 623/1.11 |
| 6,200,336 B1 | | 3/2001 | Pavcnik et al. |
| 6,241,758 B1 | | 6/2001 | Cox |
| 6,254,611 B1 | * | 7/2001 | Vrba .................... 606/108 |
| 6,379,365 B1 | * | 4/2002 | Diaz .................... 606/108 |
| 6,533,807 B2 | * | 3/2003 | Wolinsky et al. ........ 623/1.15 |
| 6,843,802 B1 | * | 1/2005 | Villalobos et al. ....... 623/1.12 |
| 6,945,989 B1 | * | 9/2005 | Betelia et al. .......... 623/1.11 |
| 2002/0052642 A1 | * | 5/2002 | Cox et al. .............. 623/1.12 |
| 2004/0029993 A1 | * | 2/2004 | Klee et al. ............. 523/113 |

FOREIGN PATENT DOCUMENTS

| | | |
|---|---|---|
| EP | 0418677 | 3/1991 |
| EP | 9415549 | 7/1994 |
| EP | 0696447 | 2/1996 |
| WO | 9618361 | 6/1996 |
| WO | 9939661 | 8/1999 |
| WO | 0156505 | 8/2001 |

OTHER PUBLICATIONS

Gianturco-Roehm Bird's Nest® Vena Cava Filter; Cook Incorporated Catalogue; 2000; 8 pages.

* cited by examiner

MEDICAL DEVICE DELIVERY SYSTEM

CROSS-REFERENCE TO RELATED APPLICATIONS

This application claims priority of provisional application Ser. No. 60/338,714, filed Nov. 29, 2001.

TECHNICAL FIELD

This invention relates to medical devices and in particular to a delivery system for delivering a medical device to a selected site.

BACKGROUND OF THE INVENTION

Delivery systems have been known for many years, for use with the Seldinger technique and related percutaneous entry techniques for vascular delivery of implants into the vasculature of human or veterinary patients. Such systems typically utilize a wire guide inserted into the vasculature to extend to the site of implantation of a medical device such as a stent, stent graft, filter, occluder, valve or the like. An introducer sheath is placed over a portion of the guide wire, and a catheter inserted over the guide wire within the introducer sheath and beyond its distal tip, with the implant contained within a distal portion of the catheter until the implant is delivered to the site of implantation. The implant is then released from the catheter distal tip and deployed. The insertion and progress of the procedure are monitored closely through fluoroscopy, angiograms or CT scanning or the like, in which radiopaque markers are commonly used as landmarks on the wire guide, catheter and implantable device to assure eventual accurate positioning of the device at the site of implantation and its full deployment.

One delivery system is known from U.S. Pat. No. 4,494,531 for delivery of a vena cava filter into the vena cava of the vasculature. The system includes a wire guide with a handle, and a cartridge catheter contains the filter at its distal end in a reduced diameter confinement and having a rear assembly. Once access is gained to the vasculature by an introducer sheath and a dilator, and the dilator is removed from the sheath, the cartridge catheter is inserted through the sheath until its distal end reaches the deployment site, whereafter the collapsed filter is deployed by gradually retracting the catheters distal end, while the filter is held axially fixed by a positioning wire guide extending to the proximal end of the filter, to initially expose the distal end of the filter having outwardly curving struts with barbs. The exposed filter then expands so that its distal barbs engage and seat in the vessel wall in cooperation with sharp, forward jabs or manipulation of the catheter, and then the remainder of the filter forms a "bird's nest" and its proximal barbs engage and seat in the vessel wall to anchor the filter in position as the catheter continues to be retracted. The particular filter disclosed in the patent is sold by Cook Incorporated, Bloomington, Ind. as the Gianturco-Roehm BIRD'S NEST Vena Cava Filter.

Delivery systems for filters are also disclosed in U.S. Pat. Nos. 5,329,942 and 5,324,304, wherein the filter is released at the deployment site by retraction of the catheter distal end from therearound as the proximal filter end is held in place axially.

It is desired to provide a delivery system for medical devices such as vascular valves that provides for assuredly centering the distal ends of valves during deployment from the delivery catheter.

It is also desired to provide such a medical device delivery system that does not interfere with precise visualization of radiopaque markers on the medical device such as a vascular valve being implanted.

It is further desired to provide such a delivery system to have a minimized diameter for use with medical devices such as vascular valves containing lyophilized tissue that enables hydration of the lyophilized tissue at the time of delivery into the patient.

SUMMARY OF THE INVENTION

The foregoing problems are solved and a technological advance is achieved by an illustrative embodiment of a medical device delivery system of the present invention. The delivery system includes a delivery catheter having a device-containing region such as, for example, a vascular valve-containing region adjacent to its distal tip, and an inner member within the delivery catheter and movable relatively axially with respect thereto when inserted over a wire guide that is positioned in the vasculature of a patient. The inner member has a reduced diameter portion extending through the device or valve-containing region to a distal tip portion distally of the device or valve-containing region, with the distal tip portion having a maximum diameter approximately the catheter diameter at the distal end thereof. The delivery system of the present invention is particularly useful with valves providing clearance for the inner member to extend through the valve opening when the valve is in a compressed state within the device or valve-containing region of the delivery catheter.

The distal end of the inner member extends sufficiently forward of the catheter distal end and the valve to engage the vessel distally of the deployment site, and in cooperation with the nearer proximal portions of the catheter centered within adjacent portions of the vasculature thus tending to center the distal end of the delivery catheter advantageously during valve deployment and also tending to temporarily straighten somewhat the local vessel anatomy. The compressed valve is movable with the inner member relatively axially with respect to the delivery catheter distal end upon actuation of the deployment procedure. The distal end of the valve sufficiently engages the inner member when being released from the distal end of the delivery catheter during catheter retraction to generally remain centered in the vessel and generally aligned parallel to the vessel at the deployment site. Preferably, the distal tip portion of the inner member is tapered on both its distal and proximal ends, and is advantageously atraumatic during insertion into the patient, and nonsnagging and nondisruptive as the inner member is withdrawn proximally through the valve following expansion and deployment thereof.

In another aspect, the inner member includes a small diameter radiolucent or transparent region coinciding with the valve in the device or valve-containing region such that radiopaque markers on the device or valve are easily distinguishable under fluoroscopy during positioning and deployment, as the device or valve is movable with the inner member during positioning and during deployment when the delivery catheter is retracted to expose the device or valve.

In a third aspect, the delivery system of the present invention is especially useful with devices or valves having lyophilized materials that require hydration before deployment. The inner member proximally of the device or valve-containing region is cylindrical in cross-section but containing a flattened side extending from the valve-containing region to the proximal end of the delivery system. Thus, a passageway or lumen is formed between the delivery catheter and inner member for advantageously irrigating and/or hydrating the lyophilized material. Hydration fluid such as water or saline solution is injectable into the delivery system through an injection port such as by use of a syringe, and the fluid is transmitted through the delivery catheter within the region between the flattened side of the inner member and the inner surface of the catheter wall, to reach the compressed valve in the device or valve-containing region for hydration of the lyophilized tissue. Such hydration is to be performed immediately prior to the insertion of the delivery system into the patient for placement of the valve. Alternatively, the proximal portion of the inner member can have a diameter less than the inner diameter of the delivery catheter to form a passageway or lumen significantly greater in cross-sectional area than the lumen formed by the portion of the flat inner member and the delivery catheter. As a result, greater volumes of irrigation fluid can be delivered to the contained medical device.

BRIEF DESCRIPTION OF THE DRAWING

Embodiments of the delivery system of the present invention will now be described by way of example with reference to the accompanying drawings, in which.

DETAILED DESCRIPTION

The present invention is especially useful with a valve stent of the type disclosed in U.S. patent application Ser. No. 09/777,091 filed Feb. 5, 2001. The stent valve disclosed therein comprising a "square" stent (as disclosed in U.S. Pat. No. 6,200,336) with extracellular matrix material such as small intestine submucosa (SIS) material secured thereto extending between the struts and having a valve opening or slit through the material. Such a valve stent is deliverable to the treatment site in the vasculature and is deployable without any specific control device within the delivery catheter and simply expands and self-seats in position in the vessel as the catheter distal end is retracted. The valve stent is simply held in position in the valve containing region distally of the larger diameter portion of the inner member immediately proximal thereto, thus overcoming any frictional forces by movement of the catheter inner surface as the catheter is retracted.

Figure 1:
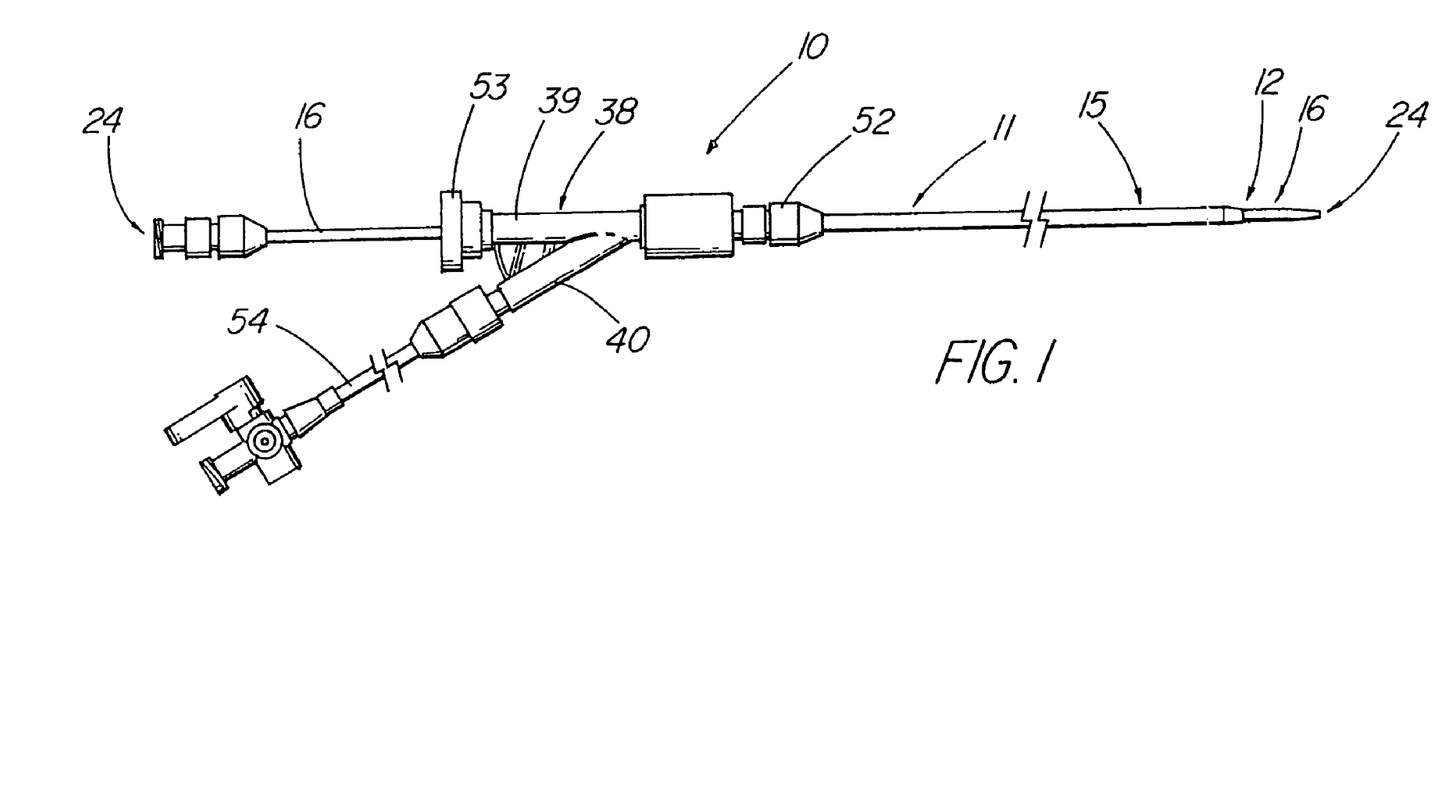
FIG. 1 depicts a top view of an illustrative preferred embodiment of the medical device delivery system of the present invention.
Figure 20:
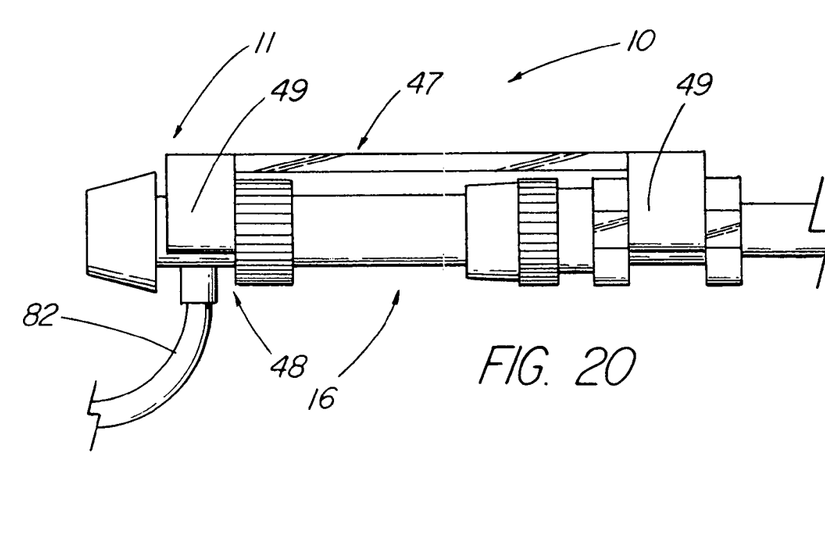

FIG. 1 depicts a top view of an illustrative preferred embodiment of medical device delivery system 10 of the present invention. The delivery system includes delivery catheter 11 having inner lumen 12 through which inner member or dilator 16 is inserted therethrough. Well-known Luer-lock connector hub 52 is affixed to the proximal end of the delivery catheter. Well-known Touhy-Borst Y-adaptor or connector 38 is connected to the connector hub of the delivery catheter through which inner member 16 is also inserted and extended therethrough. Threaded lock 53 at the proximal end of Y-connector 38 is rotated to fixedly position inner member 16 longitudinally with respect to the delivery catheter and the Y-connector. Side arm 40 of the Y-connector extends laterally at an acute angle proximally from main arm 39. Alternatively, a commercially available Check-Flo valve can be connected to connector hub 52 as depicted in FIG. 20. This valve is available from Cook Inc., Bloomington, Ind. A fluid irrigation source (not shown) is connected to side arm 40 via well-known inner interconnecting tubing and valve 54. The side arm of the Y-adaptor or connector permits the delivery of a fluid to hydrate lyophilized tissue of the medical device contained in device-containing region 15 of the delivery catheter adjacent the distal end thereof. The medical device that is contained in the delivery system of the present invention is typically delivered percutaneously to a vascular deployment site over a well-known wire guide that is inserted into the vascular system and to the deployment site. Inner lumen 24 extends longitudinally through inner member 16 as well as the delivery system, which is introduced over the wire guide through the inner lumen.

Figure 2:
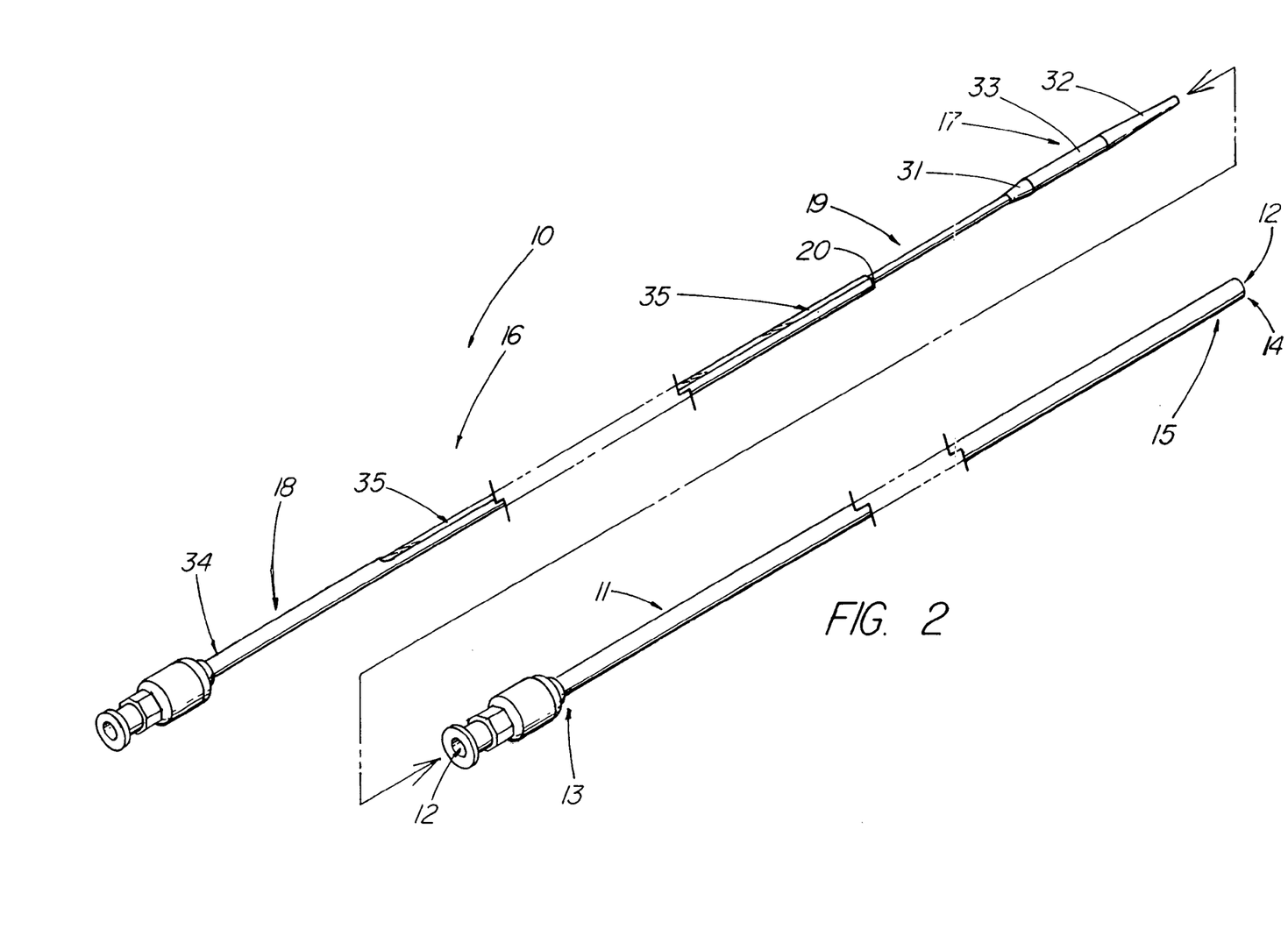
FIG. 2 depicts an exploded and enlarged view of the delivery catheter and the inner member of the delivery system of FIG. 1.

FIG. 2 depicts an exploded and enlarged view of delivery catheter 11 and inner member 16 of delivery system 10 of FIG. 1. Inner member or dilator 16 is insertable through inner lumen 12 of delivery catheter 11 that extends longitudinally between proximal end 13 and distal end 14. In particular, the inner member is also insertable through device-containing region 15 adjacent distal end 14. Inner member 16 includes a distal tip portion 17, proximal portion 18 and intermediate portion 19 disposed between the distal tip portion and the proximal portion. A medical device such as the aforementioned stent valve is positioned around the intermediate portion of the inner member. In this particular embodiment, the medical device is a stent valve including lyophilized tissue material that is affixed to a collapsible wire stent frame. The lyophilized tissue material has a slit therein through which the intermediate portion of the inner member is inserted therethrough and engages the tissue material when the stent valve is positioned around the intermediate portion. The stent valve is maintained in a compressed state or condition by delivery catheter 11 when the inner member and compressed valve are inserted therein. The assembled medical device delivery system 10 has inner member 16 extending through inner lumen 12 and beyond the distal end of delivery catheter 11. The compressed medical device is contained in device-containing region 15 of the delivery catheter adjacent distal end 14 of the delivery catheter. The compressed stent valve is deployed at the desired vascular site by maintaining inner member 16 in a stationary position and withdrawing or pulling back the delivery catheter from the intermediate portion of the inner member.

Proximal portion 18 of inner member 16 has a cylindrical outer surface 34 with a recessed or flat portion 35 extending longitudinally therealong and communicating with intermediate portion 19. This recessed or flat portion of the inner member in combination with delivery catheter 11 forms a lumen through which to hydrate the stent valve contained in the intermediate portion of the inner member. An advantage of the present invention is that reduced diameter intermediate portion 19 of the inner member is inserted through and engages the medical device for centering the medical device in the vessel in which the device is being deployed. To maintain the longitudinal position of the medical device in the vessel during deployment, proximal portion 18 of the inner member includes a blunt distal end 20 to engage the proximal end of the medical device positioned in the intermediate portion 19. This blunt distal end is also effective in holding, for example, just a stent that can be contained in device-containing region 15 and intermediate portion 19. This is most effective when the blunt distal end closely approximates the size of inner lumen 12 of delivery catheter 11.

Distal tip portion 17 of inner member 16 includes tapered proximal end 31, tapered distal end 32 and an intermediate segment 33 disposed between the tapered distal and proximal ends. The tapered distal end facilitates atraumatic placement of the delivery system to the deployment site. Tapered proximal end 31 advantageously provides atraumatic withdrawal of the inner member through the valve slit or opening after the stent valve has been deployed at the desired vessel site. Intermediate segment 33 approximates the size and shape of inner lumen 12 of delivery catheter 11 so as to provide an atraumatic transition between the assembled inner member and delivery catheter.

Figure 3:
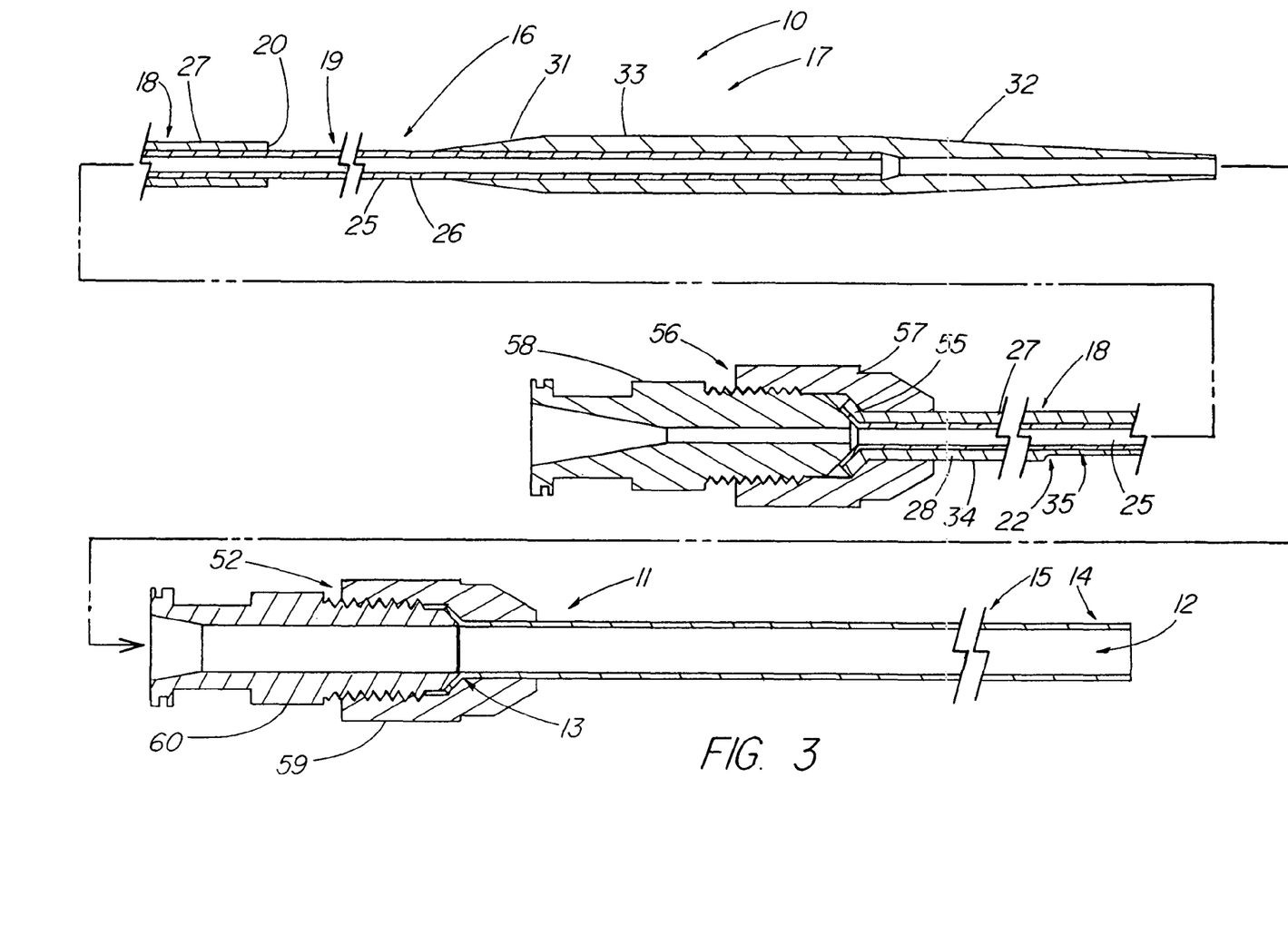
FIG. 3 depicts an enlarged and longitudinally sectioned view of the inner member and the delivery catheter of the delivery system of FIG. 2.

FIG. 3 depicts an enlarged and longitudinally sectioned view of inner member 16 and delivery catheter 11 of delivery system 10 of FIG. 2. Inner member 16 of delivery system 10 includes inner tube 25 of a radiolucent material 26 such as, for example, well-known medical grade nylon 12 polyamide material. By way of example, inner tube 25 is approximately 77 cm in length with an outside diameter of approximately 0.059 inches, an inside diameter of approximately 0.040 inches, and a wall thickness of approximately 0.0095 inches. This inner tube extends almost the entire length of the inner member through proximal portions 18, intermediate portion 19 and distal tip portion 17. The translucent material of the inner tube through intermediate portion 19 of the inner member advantageously provides better fluoroscopic visualization of the stent valve contained therearound. The radiolucent material provides very little, if any, interference with the heavier density stent, stent valve material or radiopaque markers thereon.

Inner member 16 also includes outer tube 27 coaxially positioned around inner tube 25. For all practical purposes, outer tube 27 designates the proximal and distal ends of proximal portion 18 of the inner member. By way of example, outer tube 27 is approximately 70 cm in length with an outside diameter of approximately 0.117 inches, an inside diameter of approximately 0.062 inches, and a wall thickness of approximately 0.0275 inches of a radiopaque material 28 such as well-known nylon 12 polyamide material filled with a high density radiopaque filler material such as tungsten, barium, bismuth, and the like. Outer surface 34 of outer tube 27 includes a recessed or flat portion 35 which forms a fluid lumen with the delivery catheter to hydrate a medical device positioned around intermediate portion 19. This recessed or flat portion 35 is skived into the outer surface of the outer tube approximately 0.012 inches. This recessed or flat portion extends from proximal end portion 18 of the inner member and outer tube and communicates with intermediate portion 19. Proximal end 55 of the inner and outer tubes are, for example, thermally attached and flared in a well-known manner for connection to well-known Luer-lock connector hub 56 having threaded female and male parts 57 and 58. Blunt distal end 20 of outer tube 27 is advantageously used to engage the proximal end of a medical device contained around intermediate portion 19.

Distal tip section 17 of inner member 16 includes tapered proximal end 31, tapered distal end 32 and intermediate segment 33 disposed therebetween. By way of example, the distal tip section is preferably 4.5 cm in length with an outside diameter of approximately 0.117 inches, which is approximately the same as the outside diameter of outer tube 27. The distal tip portion 17 can range in length from approximately 1.25 cm to 7 cm. By way of further example, tapered proximal end 31 can range in length from approximately 2.5 mm through 10.0 mm with a preferred length of approximately 5.0 mm. If the tapered proximal end is too short, there will be difficulty in retracting the distal tip portion through the valve orifice or slit. In addition, there can be possible induced migration of the valve along with possible damage to the valve itself. Should the tapered proximal end be too long, there is the possibility of wedging the valve between the distal tip portion and the delivery catheter. A taper that is too long may also lead to difficulties with deployment of the stent valve.

Straight intermediate segment 33 can range from approximately 0.0 through 3.0 cm with a preferred length of approximately 2.0 cm. Should the straight intermediate segment be too short, elastic deformation of the distal tip portion during forward or reverse motion over a wire guide can lead to poor delivery catheter/inner member transition or the exposure of the valve chamber and valve. Should the straight intermediate segment 33 be too long, this can lead to difficulties with deployment.

Tapered distal end 32 can range in length from approximately 1.0 through 3.0 cm with a preferred length of 2.0 cm. Should tapered distal end 32 be too short, there is the possibility of more trauma to the patient and less optimal performance and trackability of the delivery system. A tapered distal end that is too long can create production difficulties or lead to difficulties with device deployment. As depicted, the distal end of the inner tube 25 extends through tapered proximal end 31 and into straight intermediate segment 33. By way of example, the diameter of the passageway through these segments is approximately 0.059 inches approximating the outside diameter of inner tube 25. A well-known medical grade adhesive is applied to the outside surface of inner tube 25 about the distal end thereof to fixedly attach the distal end portion thereto. The remaining portion of the lumen extending through the distal tip portion is approximately 0.038 inches to accommodate a 0.038 inch wire guide. Distal tip portion 17 is formed from a well-known radiopaque nylon 12 polyamide material such as described for outer tube 27.

Delivery catheter 11 comprises, for example, a 9.0 French cylindrical tube of radiopaque fluorinated ethylene propylene (FEP) approximately 60 cm in length with an outside diameter of approximately 0.141 inches, an inside diameter of approximately 0.121 inches, and a wall thickness of approximately 0.010 inches. Luer-lock connector hub 52 comprises well-known threaded female and male connector parts 59 and 60, which are affixidly attached to flared proximal end 13 of delivery catheter 11. Device-containing region 15 of the delivery catheter is adjacent distal end 14 of the delivery catheter through which inner lumen 12 extends longitudinally therethrough.

Figures 3A, 4:
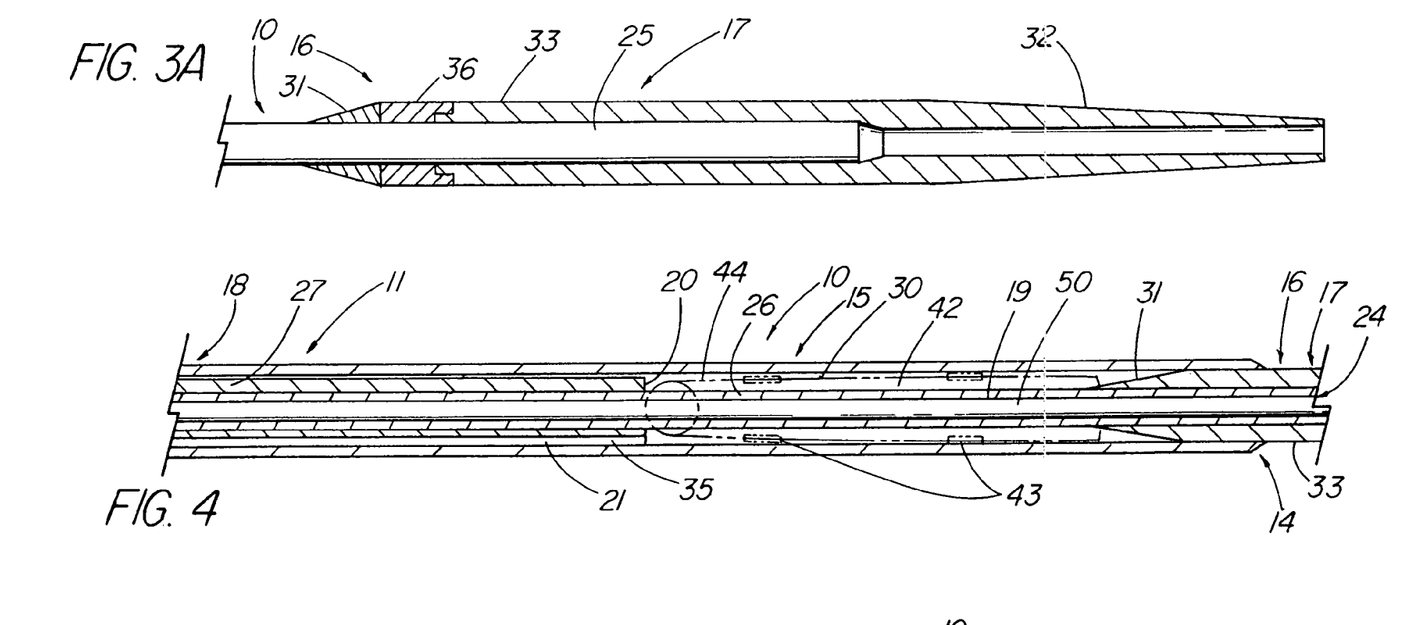
FIG. 3A depicts an enlarged and longitudinally sectioned view of an alternative embodiment of the distal tip portion of the inner member of the delivery system of FIG. 2.
FIG. 4 depicts an enlarged partial and longitudinally sectioned view of the inner member inserted through the delivery catheter of the delivery system of FIG. 3 with a medical device contained therein.

FIG. 3A depicts an enlarged and longitudinally sectioned view of an alternative embodiment of distal tip section 17 of inner member 16 of delivery system 10 of FIG. 3. Similar to FIG. 3, distal tip section 17 of this alternative embodiment includes a translucent inner tube 25 extending into the passageway of the distal tip section. However, distal tip section 17 of this alternative embodiment includes a radiopaque marker band 36 positioned at the proximal end of intermediate segment 33. The distal end of the marker band is counterbored to engage a recessed flange at the proximal end of intermediate segment 33. The marker band is disposed next to the intermediate segment over inner tube 25 and held in position with, for example, a medical-grade adhesive or glue such as a commercially available ultraviolet curable glue like Loctite 3311 glue. This glue can be shaped to form tapered proximal end 31. Alternatively, tapered proximal end 31 can be made part of and/or formed with radiopaque marker band 36. As a result, the radiopaque marker band is radiographically visualized so that delivery catheter 11 and distal tip portion 17 of inner member 16 can be visualized during the separation or joining thereof during the delivery process.

FIG. 4 depicts an enlarged partial and longitudinally sectioned view of inner member 16 inserted through delivery catheter 11 of delivery system 10 of FIG. 3 with medical device 30 contained therein. The medical device such as the previously described stent valve is positioned around and engaging intermediate portion 19 of the inner member. The medical device is maintained in a compressed condition around the intermediate portion of the inner member by delivery catheter 11, and in particular, device-containing region 15 adjacent distal end 14 of the delivery catheter. Distal end 14 of the delivery catheter is positioned around intermediate segment 33 of distal tip portion 17 of the inner member. The distal end of the delivery catheter is beveled to facilitate a smooth transition between intermediate segment 33 of the distal tip portion of the inner member. Tapered proximal end 31 of the distal tip portion of the inner member extends to intermediate portion 19 and provides for a smooth atraumatic withdrawal of the inner member through the slit or orifice of the stent valve medical device when deployed in a vessel.

Proximal portion 18 of the inner member includes distal end 20 that is sized approximating the inner lumen of the delivery catheter at least through device-containing region 15. The distal end of the proximal portion engages the proximal end of medical device 30 and maintains the medical device in a fixed longitudinal position during withdrawal of the delivery catheter during deployment of the medical device. As previously suggested, the outer surface of the proximal portion and outer tube 27 includes recessed portion 35 that cooperates with the delivery catheter to form irrigation lumen 21 for hydrating lyophilized tissue material 42 of stent valve medical device 30. This irrigation lumen extends from the proximal end region of the inner member to intermediate portion 19. As also previously suggested, medical device 30 includes wire frame stent 44 with lyophilized tissue material 42 attached thereto. Radiopaque markers 43 are positioned on the wire frame segments of the stent for fluoroscopic visualization of the stent valve during placement of the device in the vasculature of a patient. Intermediate portion 19 of inner member includes radiolucent material 26 to further improve the fluoroscopic visualization of the stent valve medical device. Inner lumen 24 extending longitudinally through the delivery device and, in particular, inner member 16 is used for guiding the delivery system over a well-known guide wire to the deployment site in the vascular system of the patient. Guide wire 50 extends through inner lumen 24.

Figure 4A:
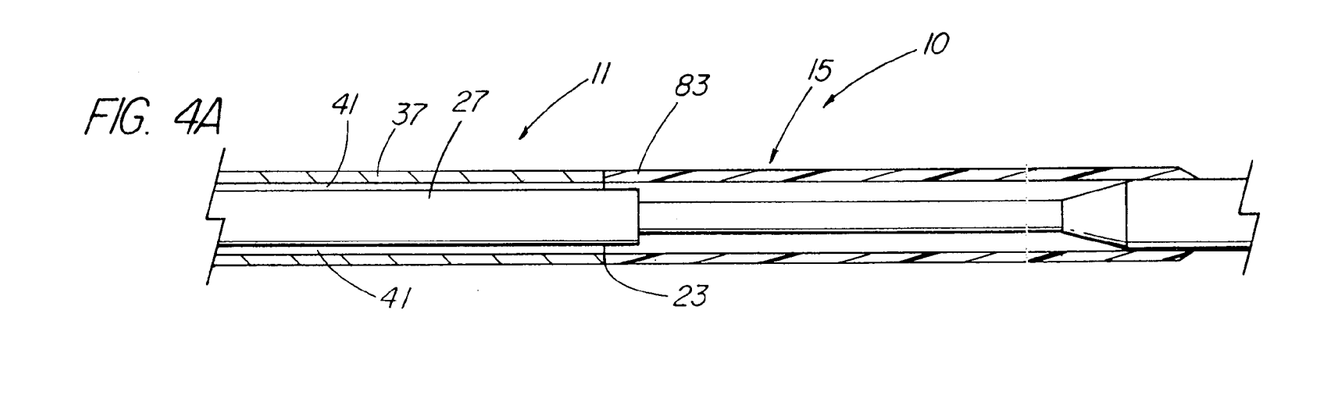
FIG. 4A depicts an enlarged partial and longitudinally sectioned view of an alternative embodiment of the delivery catheter of the delivery system of FIG. 3 with an inner member positioned therethrough.

FIG. 4A depicts an enlarged partial and longitudinally sectioned view of an alternative embodiment of delivery catheter 11 of delivery system 10 of FIG. 4 with inner member 16 inserted therein. Delivery catheter 11 comprises a cylindrical tube 37 of, for example, a radiopaque fluorinated ethylene propylene material with a device-containing region 15 of a cylindrical tube 83 of a clear or transparent non-radiopaque fluorinated ethylene propylene material thermally bonded to radiopaque tube 37 at the distal end thereof. The two tubes are thermally bonded at tapered bonding area 23. The strength of the thermal bond is improved by tapering the one end of one tube and correspondingly beveling the matching end of the other tube. The transparent tube allows for visual inspection of the medical device such as a venous valve contained within region 15 of the delivery catheter and around the recessed portion of inner member 16. In addition, the transparent tube 83 allows a check for migration, for example, of a medical device containing lyophilized small intestine submucosa which is used, for example, in a venous valve. Not only can hydration be verified through the transparent tube, but a visual check can also be made to verify the absence of air emboli in the catheter. In this alternative embodiment depicted in FIG. 4A, coaxial outer tube 27 has been reduced in its outer diameter by one French size so as to create an approximately 0.017 to 0.018 inch difference from that of the previously described embodiment. As a result, recessed or flat portion 35 is no longer needed since the outer tube is smaller in its outer diameter thus allowing for an irrigation or hydration lumen 41 to be created between inner member 16 and delivery catheter 11.

Figure 5:
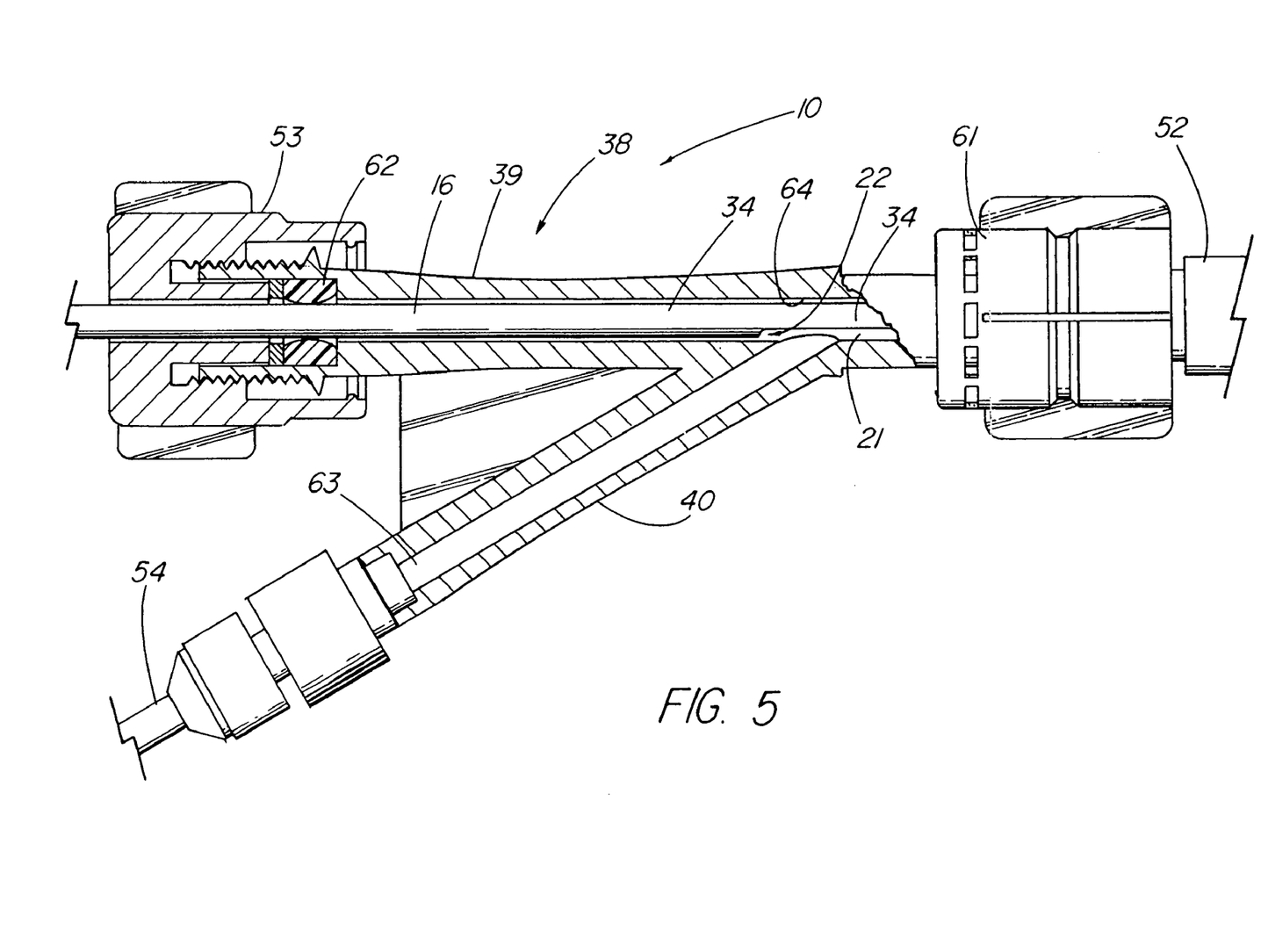
FIG. 5 depicts an enlarged and partially sectioned side view of the Y-adaptor or connector of the medical device delivery system of FIG. 1.

FIG. 5 depicts an enlarged and partially sectioned side view of Y-adaptor or connector 38 of medical device delivery system 10. Distal connector 61 of the Y-adaptor is connected to Luer-lock connector hub 52 of the delivery catheter. Threaded lock 53 is positioned at the proximal end of the Y-adaptor for fixedly positioning inner member 16 longitudinally therein. The inner member extends through main arm 39 of the Y-adaptor and through the delivery catheter. The threaded parts of threaded lock 53 compress well-known flexible polymeric material seal 62 to engage and fixedly position the inner member. In addition, flexible polymeric material seal 62 also forms a hemostatic seal at the proximal end of main arm lumen 64 for preventing blood flow from the patient. Y-adaptor 38 also includes side arm 40 connected to interconnecting tubing and valve 54. The side arm includes irrigation lumen 63 extending longitudinally therethrough and communicating with main arm lumen 64. Inner member 16 is longitudinally positioned in main arm lumen 64 such that proximal end region 22 with recessed or flat portion 35 is in communication with side arm lumen 63. The recessed portion of outer surface 34 of the inner member in combination with the inner lumen of the delivery catheter and Y-adaptor forms irrigation lumen 21 for hydrating the lyophilized tissue material of the stent valve medical device contained around the intermediate portion of the inner member.

Figures 6, 7:
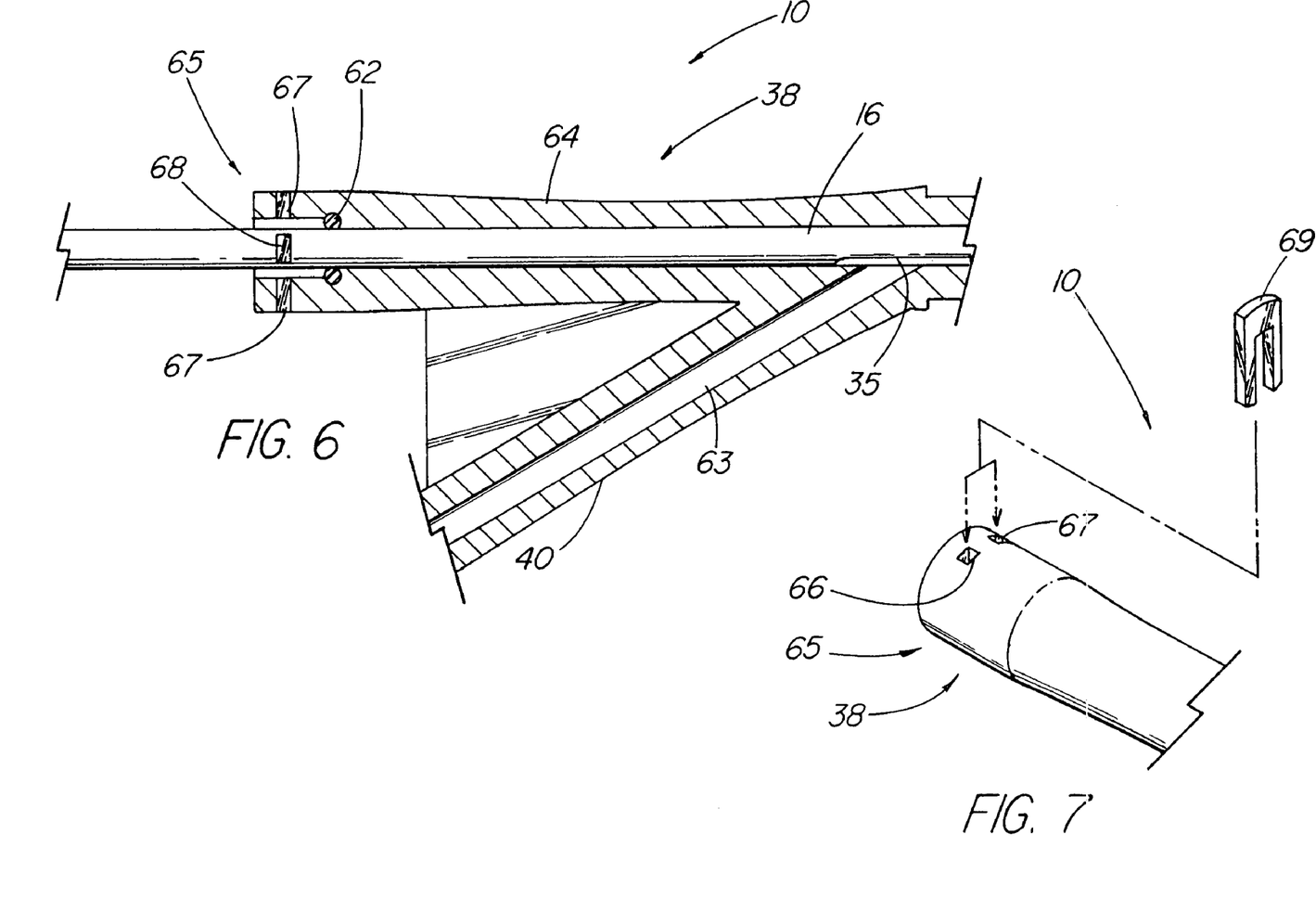
FIGS. 6 and 7 depict an alternative embodiment of the Y-adaptor or connector of the delivery system of FIG. 5.

FIGS. 6 and 7 depict an alternative illustrative embodiment of Y-adaptor or connector 38 of delivery system 10 of FIG. 5. Here again, inner member 16 extends longitudinally through main arm lumen 64 as previously described with recessed or flat portion 35 in fluid communication with side arm lumen 63. Flexible polymeric material seal 62 now takes on the form of an O ring to facilitate a hemostatic seal between the inner member and the Y-adaptor. At proximal end 65 of the Y-adaptor are apertures 66 and 67 extending transversely therethrough. A pair of transversely oriented, diametrically facing slots 68 are formed in inner member 16, which align with apertures 66 and 67 of the Y-adaptor. Two prong key 69 is inserted through the apertures and slots for fixedly positioning the inner member relative to the Y-adaptor. This fixedly positions the inner member with respect to the Y-adaptor not only longitudinally but also circumferentially. This advantageously maintains the position of recessed or flat portion 35 of the inner member with respect to the side arm lumen of the Y-adaptor. In addition, this is also utilized in combination with other structures which will be described hereinafter to rotationally fix the position of the stent valve medical device contained at the distal end of the delivery catheter.

Figures 8, 10:
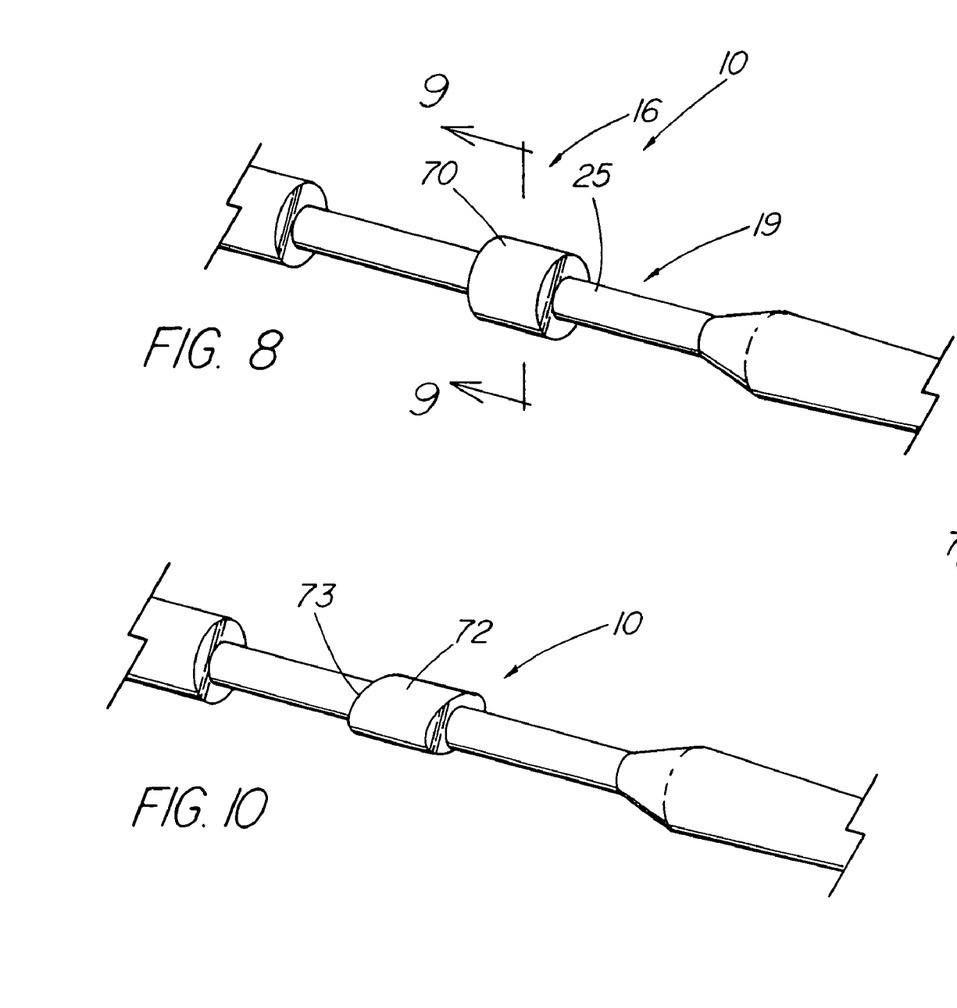
FIG. 8 depicts an alternative embodiment of the inner member of the delivery system of FIG. 1, which can be used in combination with the Y-adaptor embodiment of FIGS. 6 and 7.
FIG. 10 depicts another illustrative embodiment of the positioning arrangement of the delivery system of FIG. 8.

FIG. 8 depicts an alternative illustrative embodiment of inner member 16 of delivery system 10 of FIG. 1, which can be used in combination with the Y-adaptor embodiment of FIGS. 6 and 7. Positioned around intermediate portion 19 and, in particular, inner tube 25 is a cylindrical ring 70 of a flexible atraumatic material such as silicone and the like. This cylindrical ring of flexible material is positioned near the center of the intermediate portion of the inner member so as to engage wire frame segments or members of the stent valve medical device contained in the delivery system.

Figure 9:
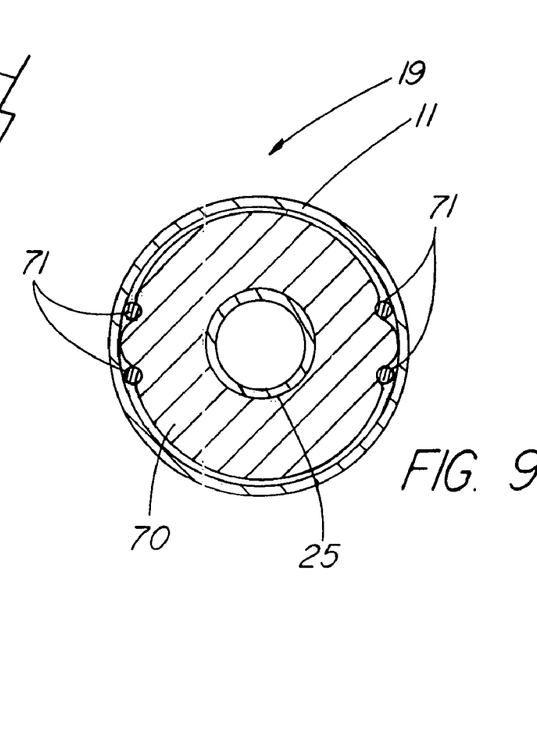
FIG. 9 is a cross-sectional view of the cylindrical ring of the intermediate portion 19 of FIG. 8 taken along the line 9-9.

FIG. 9 depicts a cross-sectional view of cylindrical ring 70 of intermediate portion 19 of FIG. 8 taken along the line 9-9 containing wire frame members 71 in delivery catheter 11. As depicted, cylindrical ring 70 is circumferentially positioned around inner tube 25 with delivery catheter 11 surrounding cylindrical ring 70 and wire frame members 71 of the contained medical device. As a result, the stent valve medical device of the present device is fixedly positioned circumferentially and longitudinally in the delivery system. Thus, the key at the proximal end of the Y-adaptor of FIGS. 6 and 7 can be used to visually indicate the rotational orientation of the stent valve medical device contained in the delivery catheter at the distal end of the delivery system.

FIG. 10 depicts another illustrative embodiment of the positioning arrangement of delivery system 10 of FIG. 8. In this alternative embodiment, the positioning member comprises a sleeve 72 having a cross-sectional shape with an elliptical circumference 73. As a result, the wire frame members or segments of the stent valve are positioned on either side of the major axis of the elliptically shaped sleeve. The orientation of the sleeve is aligned with that of the lock on the proximal end of the inner member to provide visual orientation of the stent valve contained at the distal end of the delivery system.

Figure 11:
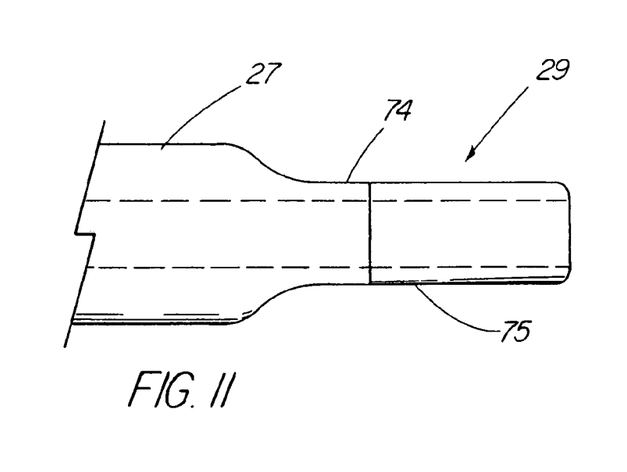
FIGS. 11 and 12 depict top and side views of still another illustrative embodiment of a positioning member of the delivery system of FIG. 1 in which the distal end of the outer tube is shaped to engage the proximal end of a stent valve medical device.
Figure 12:
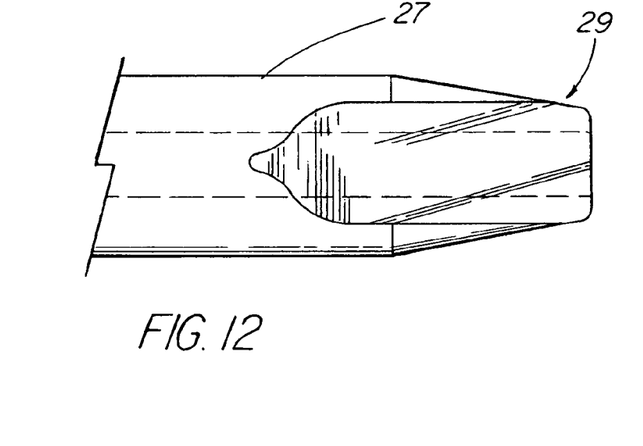

FIGS. 11 and 12 depict top and side views of still another illustrative embodiment of a positioning arrangement of the delivery system of FIG. 1 in which distal end 29 of outer tube 27 is shaped to engage one end of the stent valve medical device. In FIG. 11, the top and bottom of outer tube 27 have been skived or recessed so as to allow the wire frame segments to reside on either side of the tube. Recessed portions 74 and 75 engage the wire frame members of the device when contained in the delivery catheter. FIG. 12 depicts a top view of the outer tube with the sides of the tube beveled or tapered to form a duckbill configuration.

Figure 13:
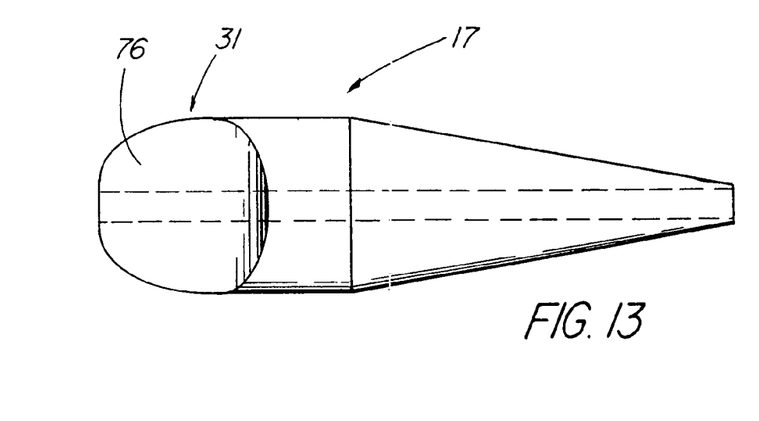
FIGS. 13 and 14 depict top and side views of another illustrative embodiment of the distal tip portion of the inner member of the delivery system of FIG. 1.
Figure 14:
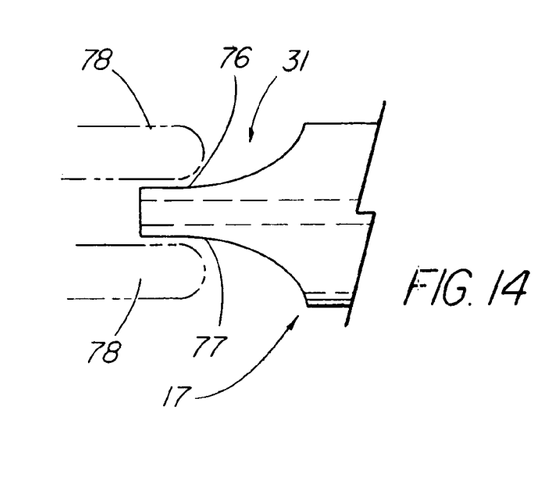

FIGS. 13 and 14 depict top and side views of another illustrative embodiment of distal tip portion 17 of the inner member of the delivery system of FIG. 1. In this embodiment, the proximal end 31 of the distal tip portion has been recessed on both sides as indicated by curvilinear surfaces 76 and 77. As depicted in FIG. 14, these curvilinear surfaces allow the other end as indicated by phantom lines 78 of the stent valve medical device to reside on the oppositely facing surfaces. As depicted in the top view of FIG. 13, the proximal end of curvilinear surface 76 has been rounded to minimize trauma or damage to surrounding tissue or the lyophilized tissue material of the stent valve.

Figure 15:
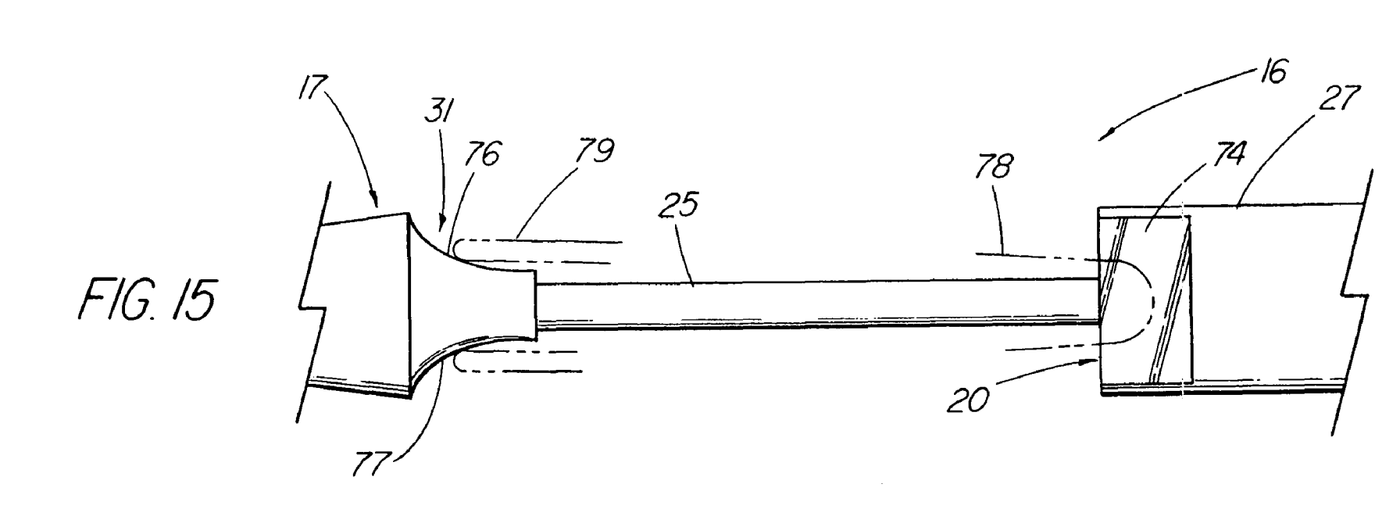
FIGS. 15 and 16 depict top and side views of still yet another embodiment of the inner member of the delivery system of FIG. 1.
Figure 16:
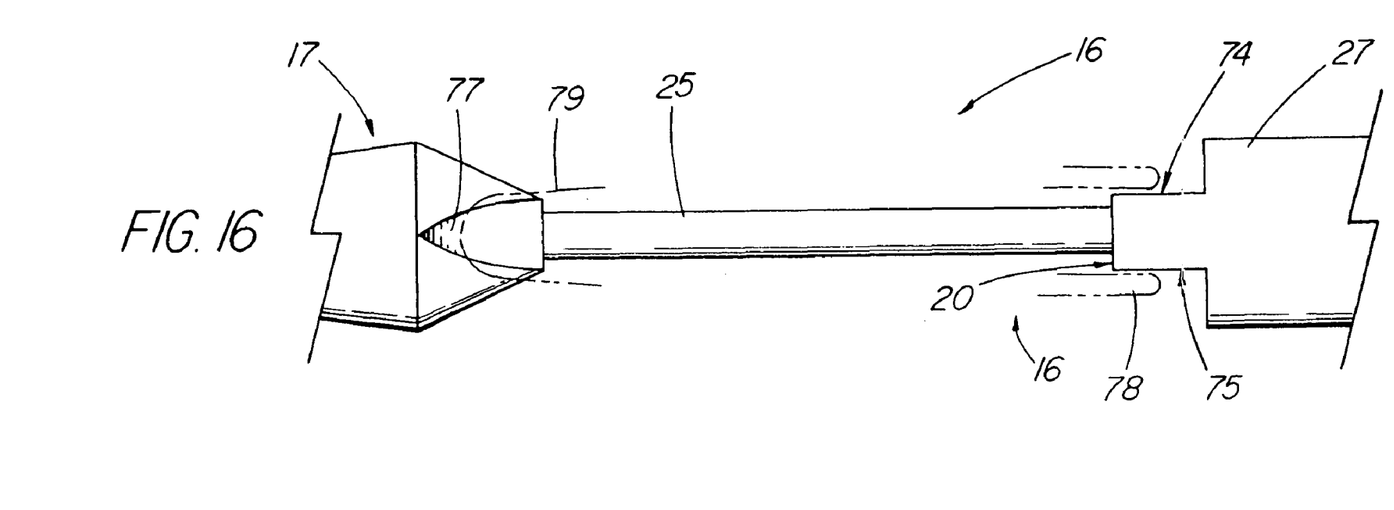

FIGS. 15 and 16 depict top and side views of still yet another embodiment of inner member 16 of the delivery system of FIG. 1. In the top view of FIG. 15, proximal end 31 of distal tip portion 17 includes oppositely facing curvilinear surfaces 76 and 77. Distal end 20 of outer tube 27 has oppositely facing recessed surfaces 74 and 75. Distal tip portion 17 and outer tube 27 are circumferentially positioned on inner tube 25 such that curvilinear 76 and 77 are 90 degrees out of phase with respect to oppositely facing recessed surfaces 74 and 75. In this positioning arrangement, the 90 degrees out of phase ends as indicated by phantom lines 78 and 79 of the wire frame stent are engaged by and contained by the recessed surfaces.

Figure 17:
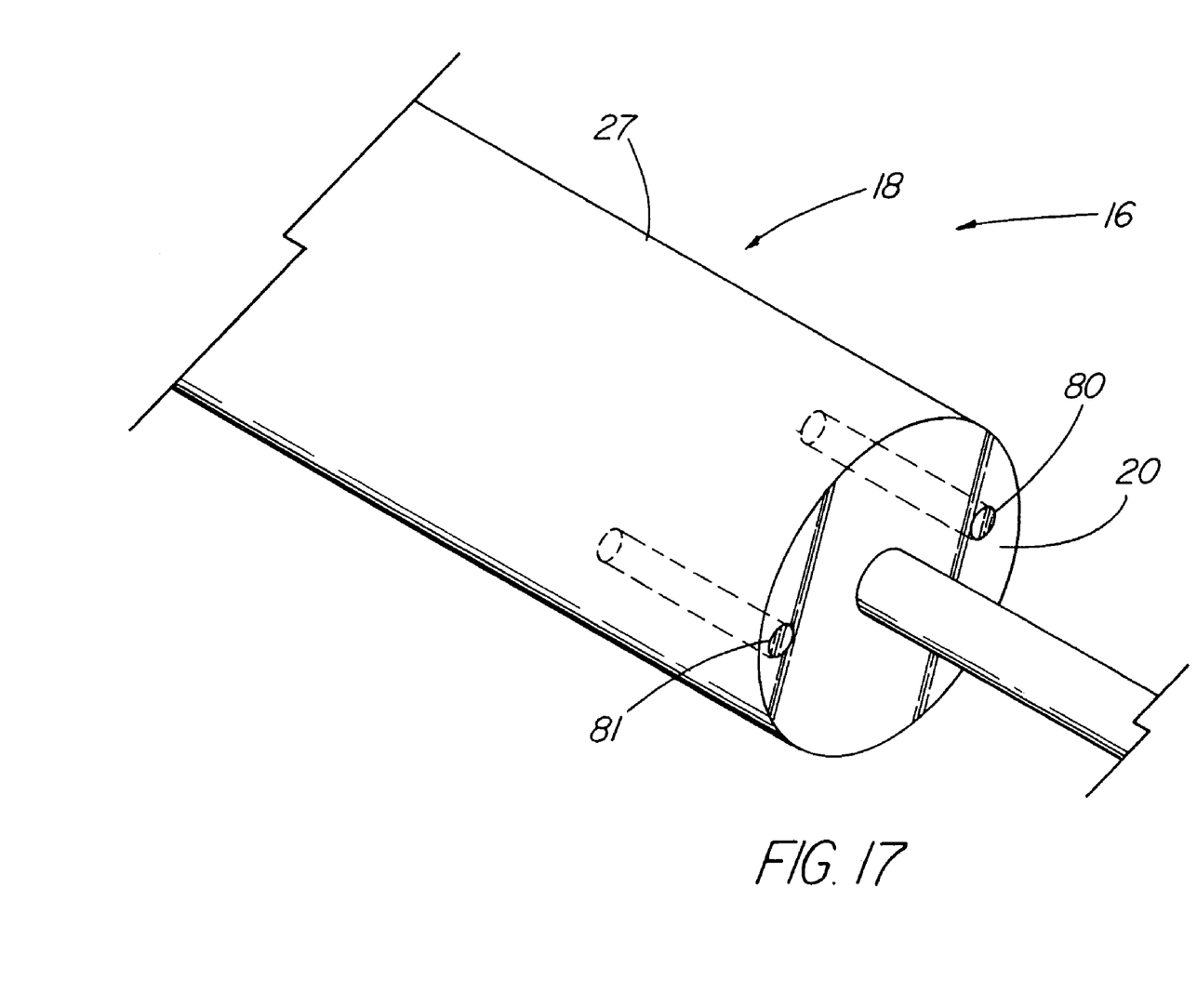
FIG. 17 depicts a pictorial view of still yet another embodiment of the inner member of the delivery system of FIG. 1.

FIG. 17 depicts a pictorial view of still yet another embodiment of inner member 16 of the delivery system of FIG. 1. To help fluoroscopically visualize the orientation of distal end 20 of proximal portion 18, two elongated segments of radiopaque material 80 and 81 are diametrically positioned in the distal end of outer tube 27. These radiopaque markers can be used with any of the embodiments previously discussed to further visualize the orientation of the stent valve medical device or the distal end of the proximal end portion of the inner member.

Figure 18:
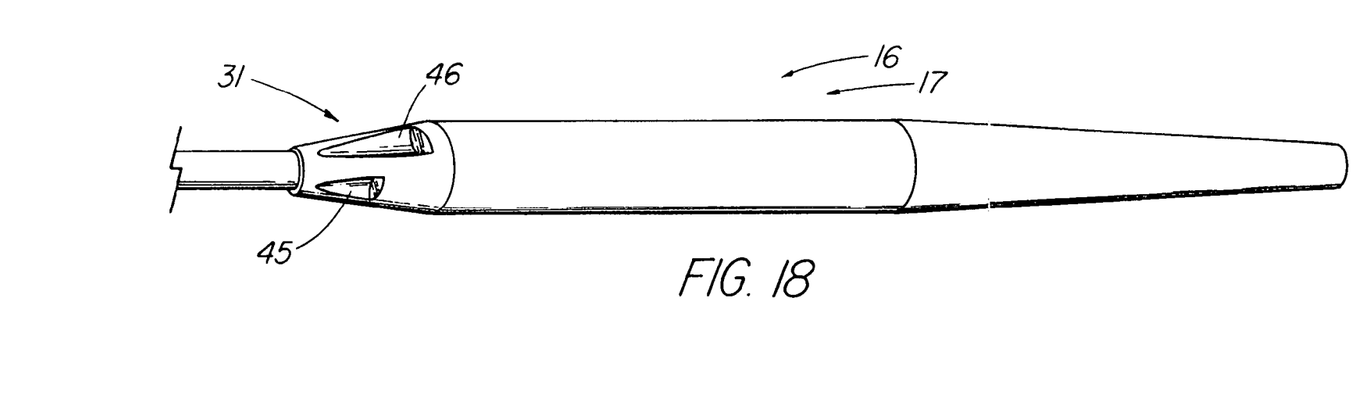
FIG. 18 depicts a pictorial view of yet still another embodiment of the inner member and, in particular, the distal tip portion of the inner member of the delivery system of FIG. 1.

FIG. 18 depicts a pictorial view of yet still another embodiment of inner member 16 and, in particular, distal tip portion 17 of the delivery system of FIG. 1. In this embodiment, tapered proximal end 31 of distal tip portion 17 includes longitudinally offset recesses 45 and 46. Offset 45 has a diametrically opposed recess on the circumference of tapered proximal end 31, whereas offset recess 46 likewise has a corresponding diametrically opposed recess on the circumference of the tapered proximal end 31. These two pairs of diametrically opposed recesses are offset from one another to accept a pair of long struts of, for example, a venous valve in recess pair 46 and to accept a pair of shorter struts in longitudinal recess pair 45. These offset recesses capture the ends of the two different length struts so as to maintain circumferential orientation of the medical device during placement. Furthermore, the medical device can be rotated with these longitudinally offset recesses for precise placement in the vasculature of a patient.

Figure 19:
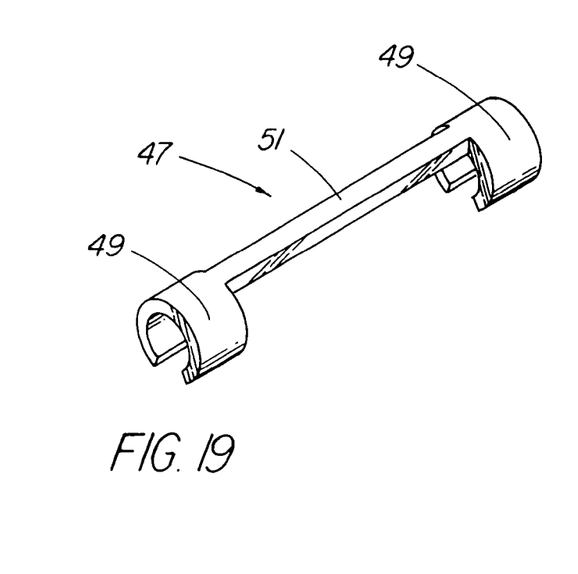
FIGS. 19 and 20 depict pictorial and side views of a locking mechanism for fixing the relative position of the inner member and delivery catheter of the delivery system of FIG. 1 in which a check flow valve is utilized instead of a side arm.

FIGS. 19 and 20 depict pictorial and side views of locking mechanism 47 of the delivery system of the present invention for fixedly positioning the relative position of delivery catheter 11 with respect to dilator or inner member 16. In this embodiment, a well-known and commercially available Check-Flo valve 48 with side arm 82 is connected to or made part of the proximal end of delivery catheter 11. This valve has an annular recess therearound as does the distal end of inner member 16, which includes a well-known Luer-lock connector hub at its distal end. To fix the relative longitudinal position of the delivery catheter and inner member, locking mechanism 47 includes a pair of C-shaped clips 49, which are interconnected by tie bar 51. The C-shaped clips of the locking mechanism are each clipped into a respective recess at the distal end of the delivery catheter and inner member so as to fix the relative position of each to one another. This locking mechanism can be readily removed by the attending physician when it is desired to withdraw the delivery catheter from the contained medical device. The locking mechanism advantageously prevents premature deployment of the medical device during the delivery and implantation procedure.

Enclosed herewith is an element list which is provided as a convenience to relate the various elements of the delivery system as depicted in the drawings and described in the detailed description. This list of elements is provided for illustrative purposes only and is not to be construed to limit the present invention in any manner.

ELEMENT LIST

| | |
|---|---|
| 10 | delivery system |
| 11 | delivery catheter |
| 12 | inner lumen of 11 |
| 13 | proximal end of 11 |
| 14 | distal end of 11 |
| 15 | device-containing region of 11 |
| 16 | inner member or dilator |
| 17 | distal tip portion of 16 |
| 18 | proximal portion of 16 |
| 19 | intermediate portion of 16 |
| 20 | blunt distal end of 18 |
| 21 | irrigation lumen of 11 and 16 |
| 22 | proximal end region of 35 |
| 23 | tapered bonding area |
| 24 | inner lumen of 16 |
| 25 | inner tube of 16 |
| 26 | radiolucent material of 25 |
| 27 | coaxial outer tube of 16 |
| 28 | radiopaque material of 27 |
| 29 | distal end of 27 |
| 30 | medical device |
| 31 | tapered proximal end of 17 |
| 32 | tapered distal end of 17 |
| 33 | intermediate portion of 17 |
| 34 | cylindrical outer surface of 18 |
| 35 | recessed or flat portion of 18 |
| 36 | radiopaque marker of 17 |
| 37 | radiopaque material tube of 11 |
| 38 | Y-connector |
| 39 | main arm of 38 |
| 40 | side arm of 38 |
| 41 | hydration lumen |
| 42 | lyophilized tissue material of 30 |
| 43 | radiopaque markers of 30 |
| 44 | wire frame stent of 30 |
| 45 | offset recesses of 31 |
| 46 | offset recesses of 31 |
| 47 | locking mechanism |
| 48 | Check-Flo valve |
| 49 | C-shaped clips of 47 |
| 50 | guide wire |
| 51 | tie bar of 47 |
| 52 | Luer-lock connector hub of 11 |

-continued
ELEMENT LIST

| | |
|---|---|
| 53 | threaded lock |
| 54 | tubing and valve |
| 55 | proximal ends of tubes 25, 27 |
| 56 | Luer-lock connector hub of 16 |
| 57 | female part of 56 |
| 58 | male part of 56 |
| 59 | female part of 52 |
| 60 | male part of 52 |
| 61 | distal connector of 38 |
| 62 | polymer material seal of 53 |
| 63 | irrigation lumen of 40 |
| 64 | main arm lumen of 38 |
| 65 | proximal end of 39 |
| 66 | apertures at 65 |
| 67 | apertures at 65 |
| 68 | slots on 16 |
| 69 | two prong key |
| 70 | cylindrical ring on 25 |
| 71 | wire frame members |
| 72 | sleeve on 25 |
| 73 | elliptical circumference of 72 |
| 74 | recessed portions at 29 |
| 75 | recessed portions at 29 |
| 76 | curvilinear surfaces of 31 |
| 77 | curvilinear surfaces of 31 |
| 78 | distal end of 30 |
| 79 | proximal end of 30 |
| 80 | radiopaque material |
| 81 | radiopaque material |
| 82 | side arm of 48 |
| 83 | clear or transparent material tube of 11 |

It is to be understood that the above-described delivery systems are merely illustrative embodiments of the principles of this invention and that other medical device delivery systems may be devised by those skilled in the art without departing from the spirit and scope of this invention. In particular, the distal end of the proximal portion of the inner member may be configured to engage the proximal end of the medical device positioned in the intermediate portion of the inner member. Furthermore, the proximal end of the distal tip portion of the inner member can be configured in any number of different ways to receive and engage the distal end of the medical device. These configurations are used to engage and rotate the medical device while still being able to determine the orientation of the medical device from the proximal end of the delivery system typically positioned outside of the patient during a percutaneous vascular procedure.

INDUSTRIAL APPLICABILITY

The present invention is useful for placement of a medical implantable device within a human or veterinary patient, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention, It is also to be understood that the invention is directed to embodiments both comprising and consisting of the disclosed parts.

What is claimed is:
1. A medical device delivery system comprising:
a delivery catheter having an inner lumen extending from a proximal end to a distal end and having a device-containing region adjacent the distal end;

an inner member extendable through the delivery catheter from the proximal end to and through the device-containing region to and beyond the distal end of the delivery catheter, the inner member having a distal tip portion, a proximal portion, an intermediate portion disposed between the distal tip portion and the proximal portion, an inner tube extending longitudinally in the proximal, intermediate, and distal tip portions, and an outer tube disposed around and fixedly attached to the inner tube in the proximal portion;

wherein the inner tube has a first flared proximal end and the outer tube has a second flared proximal end, the first flared proximal end positioned farther from the distal tip portion of the inner member on a lengthwise axis thereof than the second flared proximal end, and the first and second flared ends attached to each other so as to prevent relative movement between the inner and outer tubes; and wherein the outer tube terminates in a distal end proximal to the intermediate portion, the distal end sized approximating the inner lumen of the delivery catheter at least through the device-containing region and that engages a medical device when the medical device is positioned around the intermediate portion and in the device-containing region of the delivery catheter;

wherein the intermediate portion is extendable through the device-containing region of the delivery catheter and wherein the proximal portion includes a proximal end region and the outer tube includes an outer surface with a recess communicating with the intermediate portion and extending from the proximal end region to and including the distal end of the outer tube to form a lumen in combination with the delivery catheter through which hydration of a medical device positioned around the intermediate portion and in the device-containing region of the delivery catheter can occur; and wherein the delivery catheter is capable of being withdrawn relative to the inner member while the inner member, including the inner and outer tubes thereof, is maintained in a stationary position.

2. The delivery system of claim 1, wherein the inner tube comprises a radiolucent material.

3. The delivery system of claim 1, wherein the outer tube comprises a radiopaque material.

4. The delivery system of claim 1, wherein the distal tip portion includes a tapered proximal end communicating with the intermediate portion.

5. The delivery system of claim 1, wherein the distal tip portion further includes an intermediate segment that is sized approximating the inner lumen of the delivery catheter about the distal end thereof.

6. The delivery system of claim 1, wherein the delivery catheter includes a proximal portion having a lateral port that communicates with the recess when the outer tube is positioned in the inner lumen of the delivery catheter.

7. The delivery system of claim 1, wherein the device-containing region of the delivery catheter includes a transparent material tube.

8. The delivery system of claim 1, further comprising an implantable medical device positionable around and engageable with the intermediate portion of the inner member and containable in the device-containing region of the delivery catheter, and wherein the medical device includes a lyophilized material that requires hydration prior to deployment.

* * * * *